(12) United States Patent
Capelli et al.

(10) Patent No.: US 8,729,537 B2
(45) Date of Patent: May 20, 2014

(54) PLATFORM COMPRISING AN ORGANIC FIELD-EFFECT TRANSISTOR FOR BIOLOGICAL AND MEDICAL APPLICATIONS

(75) Inventors: Raffaella Capelli, Bologna (IT); Stefano Toffanin, Sant'angelo di Piove di Sacco (IT); Valentina Benfenati, Calderara di Reno (IT); Michele Muccini, Bologna (IT); Roberto Zamboni, Bologna (CA); Gianluca Generali, Bologna (IT)

(73) Assignee: E.T.C. S.r.l., Bologna (BO) (IT)

( * ) Notice: Subject to any disclaimer, the term of this patent is extended or adjusted under 35 U.S.C. 154(b) by 0 days.

(21) Appl. No.: 13/703,577

(22) PCT Filed: Dec. 22, 2011

(86) PCT No.: PCT/EP2011/073740
§ 371 (c)(1),
(2), (4) Date: Dec. 11, 2012

(87) PCT Pub. No.: WO2012/089608
PCT Pub. Date: Jul. 5, 2012

(65) Prior Publication Data
US 2013/0084595 A1    Apr. 4, 2013

(30) Foreign Application Priority Data
Dec. 27, 2010 (IT) .................................. MI10A2406

(51) Int. Cl.
*H01L 51/30* (2006.01)
*H01L 51/40* (2006.01)

(52) U.S. Cl.
USPC ........................................................ 257/40

(58) Field of Classification Search
USPC .................... 257/40, 59, 72, E51.006, E51, 7
See application file for complete search history.

(56) References Cited

U.S. PATENT DOCUMENTS

| | | | |
|---|---|---|---|
| 8,154,014 B2 * | 4/2012 | Tanaka et al. | 257/40 |
| 8,212,243 B2 * | 7/2012 | Shukla et al. | 257/40 |
| 8,362,474 B2 * | 1/2013 | Furukawa et al. | 257/40 |
| 8,525,156 B2 * | 9/2013 | Nakamura et al. | 257/40 |
| 2008/0054258 A1 * | 3/2008 | Koenemann et al. | 257/40 |
| 2008/0087878 A1 | 4/2008 | Koenemann et al. | |
| 2009/0032411 A1 | 2/2009 | Peitz et al. | |

FOREIGN PATENT DOCUMENTS

WO       2004/086526       10/2004

OTHER PUBLICATIONS

PCT International Search Report mailed on Mar. 5, 2012 for PCT/EP2011/073740 filed on Dec. 22, 2011 in the name of E.T.C. S.P.A.
PCT Written Opinion mailed on Mar. 5, 2012 for PCT/EP2011/073740 filed on Dec. 22, 2011 in the name of E.T.C. S.P.A.
PCT Written Opinion mailed on Nov. 21, 2012 for PCT/EP2011/073740 filed on Dec. 22, 2011 in the name of E.T.C. S.P.A.

(Continued)

*Primary Examiner* — Cuong Q Nguyen
(74) *Attorney, Agent, or Firm* — Steinfl & Bruno, LLP

(57) ABSTRACT

The present invention relates to a device comprising an organic field effect transistor (OFET) with charge injecting contacts containing a semiconductor layer formed by a perylene derivative, to uses of said device as a medical sensor and/or as a medical cell stimulator and to methods of stimulating and/or monitoring biological cellular activity by using said device.

21 Claims, 14 Drawing Sheets

(56) References Cited

OTHER PUBLICATIONS

An, MJ, et al., Air stable, ambipolar organic transistors and inverters based upon a heterojunction structure of pentacene on N,N-ditridecylperylene-3,4,9,10-tetracarboxylic ndi-imide, Appl. Physics Letters 2010, 97:023506-1-023506.

Muccini, M. A bright future for organic filed-effect transistors, Nat. Mar. 2006, 5: 605-614.

Feili, D., et al., Matrix-addressable, active electrode arrays for neural stimulation using organic semiconductiors—cytotoxicity and pilot experiments in vivo, J. Neu. Eng. 2008, 5: 68-74.

Someya, T., et al., Integration and response of organic electronics with aqueous microfluidics, Langmuir 2002, 18: 5299-5302.

Malefant, P., et al., N-type organic thin-film transistor with high field-effect mobility based on a N,N-dialky1-3,4,9,10-perylene tetracarboxylic dilmide derivative, Appl. Phys. Letters 2002, 80: 2517-2519.

Sujith, Ok, Functional electrical stimulation in neurological disorders, Euro. J. Neuro. 2006, 15: 437-444.

Poghossian, A., et al. Field-effect devices for detecting cellular signals, Seminar in Cell & Develop. Biol. 2009, 20: 41-48.

Bystrenova, E., et al., Neural networks grown on organic semiconductors, Adv. Func. Mat. 2008, 18: 1751-1756.

Response to PCT Written Opinion mailed on Aug. 13, 2012 for PCT/EP2011/061219 filed on Jul. 4, 2011 in the name of SAES GETTERS S.P.A.

Christopher J. Bettinger et al., Organic Thin Film Transistors Fabricated on Resorbable Biomaterial Substrates, Advanced Materials, vol. 22, No. 5, Feb. 2, 2010, pp. 651-655.

Theodore R. Cummins et al., Voltage-clamp and current-clamp recordings from mammalian DRG neurons, Nature Protocols, vol. 4, No. 8, 2009, pp. 1103-1112.

International Preliminary Report on Patentability of PCT Application PCT/EP2011/073740 filed on Dec. 22, 2011 in the name of E.T.C. S.r.l., mailed on Dec. 19, 2012.

\* cited by examiner

PLATFORM COMPRISING AN ORGANIC FIELD-EFFECT TRANSISTOR FOR BIOLOGICAL AND MEDICAL APPLICATIONS

CROSS REFERENCE TO RELATED APPLICATIONS

The present application is the U.S. national stage of International Application PCT/EP2011/073740 filed on Dec. 22, 2011 which, in turn, claims priority to Italian Application MI2010A002406 filed on Dec. 27, 2010.

Organic field effect transistor (OFET) and organic light emitting transistors (OLET) are devices attracting interests in view of a broad range of possible applications and use. More details on the structure of these devices may be found in the international patent application WO2004086526 whose teachings are herein incorporated by reference.

In particular, organic semiconductor devices may be successfully used to generate organic-multi-transistor array for real-time monitoring of bioelectrical activity of neuronal cells but may also be employed for the electrical stimulation of neural cells by either direct exposure to electrical current or via an electric field has been shown to effect stem cell differentiation and neurite extension and influence directionality of growing axons.

The characteristics of the device according to the invention are really promising also out of biological context as basis platform for OFET-based sensors functional in aqueous systems with their vast potential in the health industry, environmental monitoring.

A wide variety of microfabricated devices have been developed for applications in medicine and biology as described, for example, by Poghossian et al. in the scientific publication "Field-effect devices for detecting cellular signals" on Seminars in Cell & Developmental Biology in the 2009 pagg. 41-48.

One of the key challenges in the field of bioelectronics is the development of devices that enable transduction of cell bioelectrical activity into quantitative signals; or supply of selective electrical stimuli, avoiding invasive monitoring and perturbating approaches.

These device find application in in vitro real-time monitoring of living systems or as in vivo biomedical micro-implants such as neural prostheses to restore body functions after injury by means of functional electrical stimulation. Electrical stimulation as a therapeutic treatment is a rapidly expanding area in the field of tissue engineering, especially for nerve applications, with numerous reports showing that electrical stimulation increases neurite and axon extension in vitro and nerve regeneration in vivo, as for example described by Sujith et al. in the scientific publication "Functional electrical stimulation in neurological disorders" published on the European journal of neurology in the 2008 pag. 437.

Several bio-interfaced devices based on inorganic semiconductors have already been realized. For example, multiarray electrodes and field-effect devices for electrophysiological applications in neuroscience have been fabricated and developed to the point that commercial devices are available. Recording from either neuronal single cells or slices by silicon based transistors has been reported. Moreover, high density Si nano-wire transistor arrays have been generated, enabling detection and modulation of electric signals in cardiomyocyte or in neuron at synaptic level. Despite the importance of these observations, the reported approaches face with limited sensitivity due to low capacitive coupling and require chemical coating of the surface for the attachment of neurons. Moreover, silicon-based electronic devices raise the cost of the final applications system. Finally, despite the silicon-based microelectrodes show good performance in vitro, significant biofouling and low biocompatibility have been observed in vivo for long time exposure with neural tissue.

Microelectronic systems employing organic materials show many advantages over traditional silicon-based systems. As described by Bystrenova et al. in the scientific publication "Neural Networks Grown on Organic Semiconductors" published on Advanced Functional Materials in the 2008 pagg. 1751-1756, organic electronic devices have potential manufacturing advantages including solution processing enabling large-scale fabrication with reduced cost.

When microelectronic devices are to be interfaced directly with living organism, they should satisfy two main conditions: 1) biological activity of the cell should be preserved: 2) the device should be able to operate in conditions that, at least in vitro, mimic the biological environment.

The first requirement points mainly to the organic semiconductor layer that in first instance is the interface with the biological sample, e.g. neural cells. However, neural cells are very highly organized and complex systems that require a non perturbating environment for preserving their physiological function. In particular, alteration of electrophysiological properties of neuronal cells, (i.e excitability membrane properties) by interaction with organic semiconductor should be avoided in order to obtain reliable results during device operation. Moreover, monitoring and controlling bioelectrical cell function is relevant to define mechanistic relationships between cell-interface interactions in vitro. In this context, it has to be underlined that, to date, despite data reported on growth and adhesion on organic semiconductor material, no evidence has been reported concerning the effect of organic layer on neuron firing capability or electrophysiological membrane properties underpinning neuronal biological function.

In order to comply with the second requirement described above, as taught by Bettinger et al. in the scientific publication "Organic thin-film transistors fabricated on resorbable biomaterial substrates" published on Advanced Materials in the 2010 pag. 651, devices that integrates resorbable electronically active materials have been realized for the use as temporary medical implants with electronic functionality. Moreover air stable and water stable OFET has been generated and reported.

In organic field-effect transistors (OFET) the active material is an organic semiconductor thin-film and the charge accumulation and transport occurs in the first nanometers at the interface between the organic and the dielectric layers. When cells adhere and grow on organic films in OFET, it is expected that the response of thin-film transistors can be enhanced through the close proximity of the cell membrane and the charge transport area.

Object of the present invention is therefore a device to be used in aqueous based systems, capable of improved performances with respect to the known systems and devices, and in a first aspect thereof consists of an aqueous based system sensor comprising an organic field effect transistor (OFET) with charge injecting contacts containing a layer made with a diimmide perylene derivative (PTCDI), substituted with alkyl groups at the Nitrogen atoms, according to formula (I)

Formula (I)

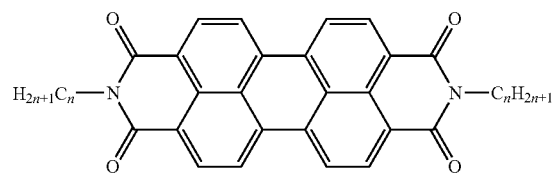

Preferably, the two alkyl groups at the nitrogen atoms of the diimmide perylene derivative of formula (I) are n-alkyl groups.

The most useful diimmide perylene derivative compounds useful to carry out the present invention have the two alkyl groups on the Nitrogen atoms with the same number of carbon atoms.

Preferably the alkyl groups have 5, 8, 12, 13, 14 or 18 carbon atoms and, even more preferably the diimmide perylene derivative is N,N'-ditridecylperylene-3,4,9,10-tetracarboxylic diimide (P13) layer.

The invention will be further illustrated with the help of the following figures and drawings, where:

Figure 1A:
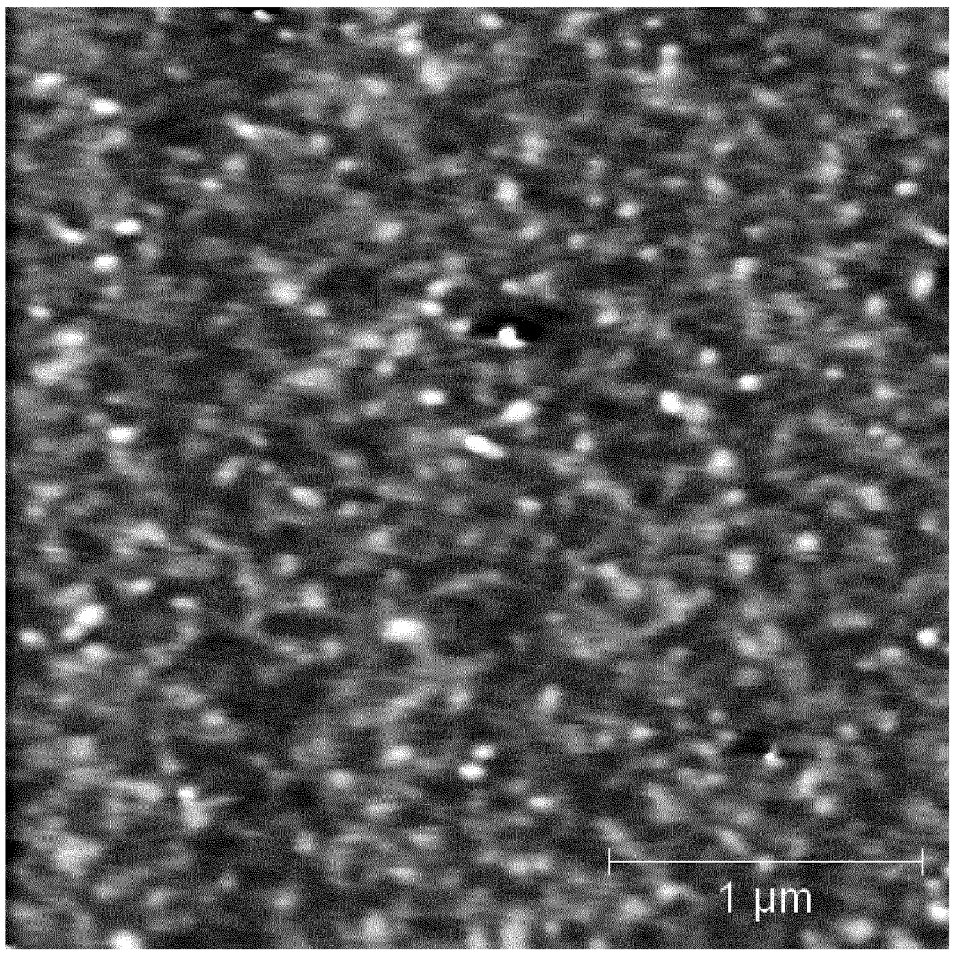
FIGS. 1A and 1B show the morphology of a P13 film.

According to an embodiment thereof, the OFET according to the present invention comprises a capping layer to protect the electrodes. Said capping layer is preferably also made of a diimmide perylene derivative (PTCDI), substituted with alkyl groups at the Nitrogen atoms, according to formula (I) or of pentacene. Preferably the capping layer is made of P13.

The maximum thickness of the capping layer shall be comprised between 35 nm and 100 nm and preferably between 40 and 70 nm. The maximum thickness is the thickness of the capping layer in correspondence of the organic semiconductor layer, while typically the thickness in correspondence of the device charge injecting electrodes is reduced by the height of these elements, since this condition will provide for a device with a uniform height. In an alternative embodiment the capping layer can be localized only in correspondence of the charge injecting contacts. This latter solution shows some drawbacks related to a required higher degree of dimensional control in the manufacturing process and also results in being less efficient in protecting boundary regions or edges, more prone to degradation.

Also, the device may further comprise on the capping layer a framing deposit, in correspondence of the OFET boundaries, made of a suitable, inert material, such as a resin and preferably an epoxy resin, in order to create a "basin" to hold the aqueous based environment under testing.

According to the invention, a novel approach and use of the technology is provided, which allows the OFET structure to be implemented for sensing biological activity or inducing functional and structural modifications in cells and, in an even more preferred embodiment, an extremely noteworthy use of the devices combines the sensing and stimulating function. As a matter of fact, with the devices described in the present invention it is possible at the same time to provide the stimulus to the cells (driving function of the device) and to monitor and observe the effect that such stimulus induces onto the cells (sensing function of the device). In an even more preferred embodiment the device is a light emitting OFET (OLET), made with a diimmide perylene derivative (PTCDI), substituted with alkyl groups at the Nitrogen atoms, according to formula (I), in which the stimulus is given by a luminous emission by the device and the sensing is given by an electrical signal or a luminous emission or a variation in the luminous emission by the device.

In particular, at present the effect of real in vitro cell culture environment i.e. 5% $CO_2$, 95% humidity and 37° C. temperature on organic electronic devices has never been successfully reported.

Diimmide perylene derivative (PTCDI), substituted with alkyl groups at the Nitrogen atoms, according to formula (I), are suitable compounds for integration in a bio-compatible devices. When employed as fluorochrome for living cells staining they displayed a good biocompatibility even with hyppocampal neurons. In addition, in recent years, perylene diimide derivatives have been used to realize stable unipolar as well as ambipolar OFETs. even though it is to be remarked, that the possibility to successfully employ these devices in a liquid environment, as later on precisely defined, was totally unexpected and unforeseen also keeping into account the particular nature of the most interesting liquid environments.

In the following part of the description usually the structures and results will be presented with reference to P13 as a perylene derivative, but it is to be understood and underlined that such compound is just an example of the most wide class of perylene derivatives that are suitable for the realization of the present invention, with reference to the diimmide perylene derivative (PTCDI), substituted with alkyl groups at the Nitrogen atoms, according to formula (I).

As aqueous based system it is intended any liquid environment to which the transistor is exposed containing a physiological solution such as real in vitro cell culture environment (i.e. 5% $CO_2$, 95% humidity and 37° C. temperature) or any environment where these conditions are retained. An aqueous based system is also aqueous based solutions for cell culturing i.e DMEM or MEM supplemented DMEM, with 10% Fetal Bovine Serum (FBS) and growth factors (as 50 ng/ml nerve growth factor (NGF), glial derived nerve growth factor or generally neurotrophines or pleiotrofines), and eventually inhibitors of specific cell proliferations (i.e. cytosine b-D-arabinofuranoside, (AraC, Sigma) (1.5 µg/ml). Addition of antibiotics (such as penicillin and streptomicine) to aqueos based system is also possible. As aqueous based system is also to be intended any saline solutions with different ion salt composition used to analyze cell bioelectrical properties (for example Ringers solution, Phosphate Buffer Saline, Artificial Crebro Spinal fluid, Standard extracellular saline).

The major findings of the present invention are the following: 1) DRG neurons adhere, grow and differentiate in dense network connection after several days (2 weeks) on P13 (N,N'-ditridecylperylene-3,4,9,10-tetracarboxylic diimide) thin-film coated with PDL+laminin layer; 2) P13 semiconductor layer preserving neuronal firing capability display fully functional biocompatibility; 3) living primary DRG neuronal cells survive on P13-OFET device 4) Surprisingly, the field-effect transport is still well performing even after several days (16) of exposure to standard condition currently applied for in vitro cell culture; 5) the complementary information from CLSM (confocal laser scanning microscopy) and AFM (atomic force microscopy) analysis performed in physiological solutions and cell culture media strongly indicated that P13 is structurally and morphologically suitable to sustain the prolonged exposure to aqueous environment that is required for experiments with living cells.

Our results clearly show that primary sensory DRG neurons from post-natal rat remain viable for many days and displayed neurite outgrowth on P13-PDL-laminin coated surfaces. Importantly. peripheral neurons grown on P13-thin film fire and retained excitability properties resembling those previously reported in the prior art, as for example by Cummins et al. in the scientific publication "Voltage-clamp and current-clamp recordings from mammalian DRG neurons" on Nature Protocols in the 2009 pagg. 1103-1112. In addition, we determine the effect of in vitro neuronal cell culture environment on P13-n-type OFET electrical performances. Surprisingly, P13-based OFET preserve their characteristics in terms of electron mobility and threshold voltage values after 16 days of in vitro treatment, showing the ability of this device to operate after interaction with 5% $CO_2$, 95% humidity and at a temperature of 37° C. (typical real in vitro condition). Of note, the morphology of P13 thin-films does not change significantly upon exposure to physiological solutions.

Collectively our results introduce a novel organic semiconductor platform based on P13 (as preferred representative of the diimmide perylene derivative (PTCDI), substituted with alkyl groups at the Nitrogen atoms, according to formula (I)) that represents an important step towards the goal of developing a fully bio-integrated organic electronic device, for cell activity transduction and electrical stimuli supply.

Cultures of dissociated rat DRG neurons is a validated model to determine the regenerative outgrowth capabilities of individual neurons of peripheral nervous system in the presence or absence of in vivo pre-nerve injured lesion. Moreover, many of the functional properties of nociceptive neurons in vivo are known to be replicated in small cultured neurons from the DRG.

Thus, we sought to culture DRG primary neurons from post-natal mice on 50 nm P13 thin films grown on glass coverslips. To ensure proper adhesion of cell preparation to the surface we treated P13 layer with Poly-D-Lysine (PDL) and laminin. The first is a polycationic molecule, currently used to allow cells, which have an overall negative surface charge, to attach to similarly charged glass surfaces. Its enantiomeric configuration enables it to withstand proteolytic activity and does not interfere with cell physiology. Laminin, a protein derived from extracellular matrix, interacts with PDL, shielding its charge and providing a more biological surface for neuronal cells.

The device performance were next evaluated before after the above described treatment at different time points, in order to verify the effect of cell culture treatment on device operation. post-treatment measurements were performed after repetitive washing with water to avoid possible effects of ionic species on the field-effect transistor behaviour.

We mentioned that in Bystrenova et al. reported that pentacene OFETs immersed in water at room temperature for several days displayed a mobility decrease by about one order of magnitude, while the threshold voltage approached asymptotically a steady state value of 35 V with a characteristic time of two days. With the devices of the present invention we have found almost no difference in mobility values before and after treatment whereas the threshold voltage rises to values comparable to those of pentacene OFET after a longer period of exposure in water (16 versus 6 days) and at a different temperature (37° C. versus RT).

Moreover, our solution has clear fundamental advantages with respect to resorbable organic devices recently described in the above mentioned publication by Bettiger et al. In fact, in that case, exposure of the device, implementing nPVA and xPVA dielectrics, to water or to phosphate buffered saline resulted in immediate device failure due to delamination of the structure.

Figure 1B:
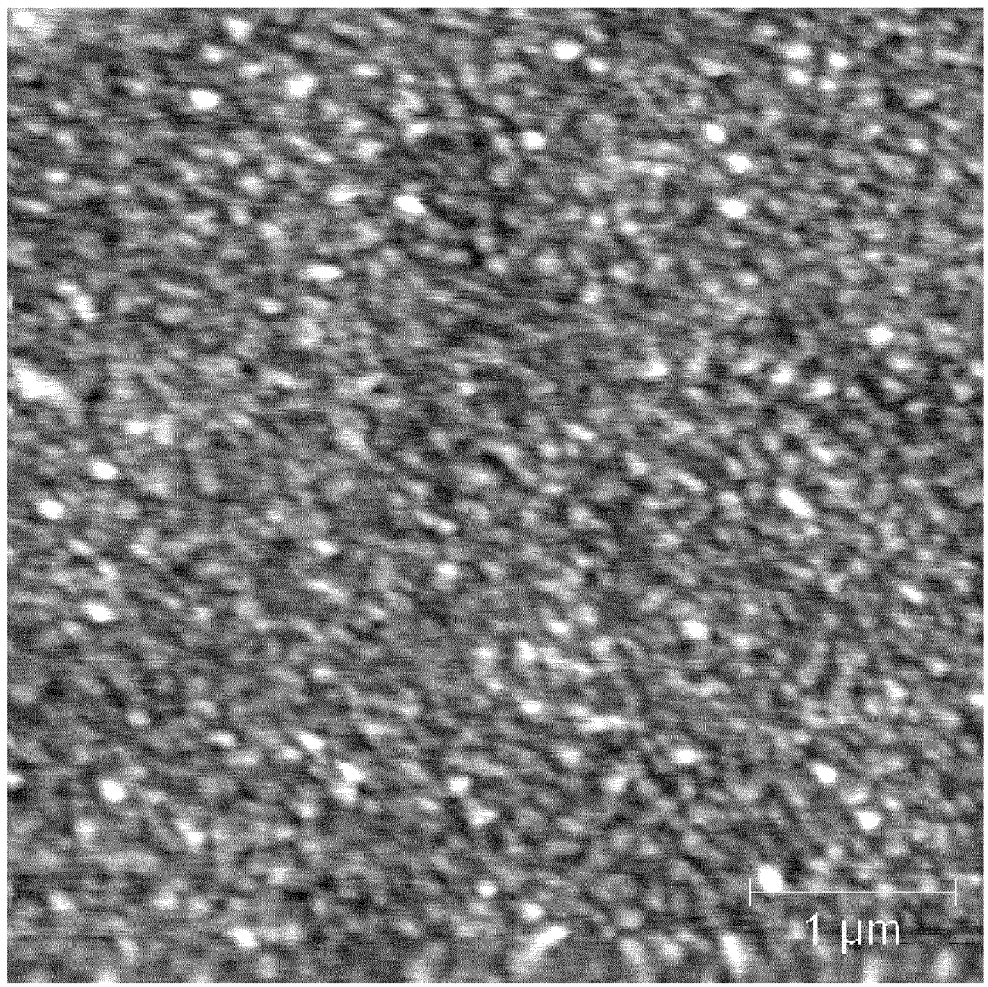

Finally, the morphology of P13 thin films upon exposure to cell culture media has been determined by performing AFM (FIG. 1). P13 film morphology is retained in DMEM-Media cell culture in the mesoscopic length scale and the rms roughness is comparable to the one measured in air (FIGS. 1A and 1B).

With the present invention it is possible to overcome a challenging step in the development of electronic transducers based on OFET. Indeed, for the first time we have proven that an organic semiconductor layer and neural cells can be coupled in a single device architecture preserving both field-effect transport and neuronal physiological firing properties.

EXAMPLE 1

N,N'-ditridecylperylene-3,4,9,10-tetracarboxylic diimide OFETs were fabricated in top-contact and bottom-gate configuration (see FIG. 2A). The substrates consisted of 1 inch square glass coated with a 150 nm-thick layer of Indium Tin Oxide (ITO) that worked as gate electrode. The substrate cleaning procedure consisted of multiple sonications of dichloromethane, acetone, ethanol and UHP water in order to remove possible organic contamination. Once the substrate was introduced in a nitrogen glove-box ($O_2$ and $H_2O$ concentration less than 1 ppm), a 600 nm-thick PMMA film was spin-coated on it. The PMMA film was then annealed for 12 h at 120° C. in the glove-box, which reduced the film thickness to about 450 nm.

P13 thin-films were grown by sublimation in high vacuum at a base pressure of 10-8 mbar in a Kurt J. Lesker Spectros chamber directly connected to a nitrogen glove-box to prevent sample air-exposure before cell plating both on PMMA/ITO/Glass and microscope coverslip substrates. The semiconductor layer had a nominal thickness of 15 nm as measured with a quartz microbalance. The growth rate was fixed at 0.1 Å/s.

In the case of P13 OFETs, Au electrodes were deposited in high vacuum at a base pressure of $10^{-6}$ mbar at a growth rate of 0.5 Å/s with the sample held at room temperature. The electrode thickness was 50 nm. The channel length and width were 70 μm and 15 mm, respectively. Electronic characterization of OFETs were performed in the glove-box using a SUSS probe-station adapted to perform optoelectronic investigations coupled to a B1500A Agilent semiconductor.

Primary cultures of DRG neurons were prepared from post natal p14-p18 rats according to commonly used protocols. Rat pups (Wistar) where anestetized by alotan and killed by decapitation. Around thirty ganglia were removed from rats, roots were cut with microdissecting scissors, and then placed in ice cold PBS. After being rinsed in Dulbecco's Modified Eagle's Medium (DMEM, Gibco), the ganglia were placed in DMEM containing 5000 U/ml type IV collagenase (Wentinghton) for 60-75 min at 37° C., 5% $CO_2$, and then dissociated gently with few passages through 0.5 mm and 0.6 mm sterile needles. Cells were washed twice by re-suspension and centrifugation and then appropriately diluted in 1 ml of DMEM medium containing 10% Fetal Bovine Serum (FBS). Cell suspension was dropped onto 19 mm round. glass coverslips on which 50 nm of P13 thin films was grown or on the top of P13-OFET device. Films or device were pre-coated with 50 mg/ml poly-D-lysine, followed by 10 mg/ml laminin (Sigma), and placed in a 37° C., 5% $CO_2$ incubator. Cells were maintained in DMEM, Gibco added with 10% FBS in the presence of 50 ng/ml nerve growth factor (NGF), and cytosine b-D-arabinofuranoside, (AraC, Sigma) (1.5 µg/ml) to reduce glial cell expression. Cell culture was optically visualized after 3 days, 5 days, 9 days and 15 days in vitro (div), by optically imaging with a Nikon Eclipse 2000-E laser scanning confocal microscope equipped with a 20× oil-objective and Hamamatsu ORCA CCD camera. Images reported are representative of 3 different cell culture preparations.

DRG cell culture plated on P13-OFET were mounted in a custom made sample holder and incubated for 5 min with fluorescein diacetate (Sigma Aldrich). After rinsing with physiological saline solution a sequence of confocal laser scanning images were taken using a Nikon Eclipse 2000-E laser scanning confocal microscope (40× oil-objective). Fluorescence of the cells plated on P13 OFET and the Photoluminescence signal of P13 film were collected through the glass substrate.

Figure 3:
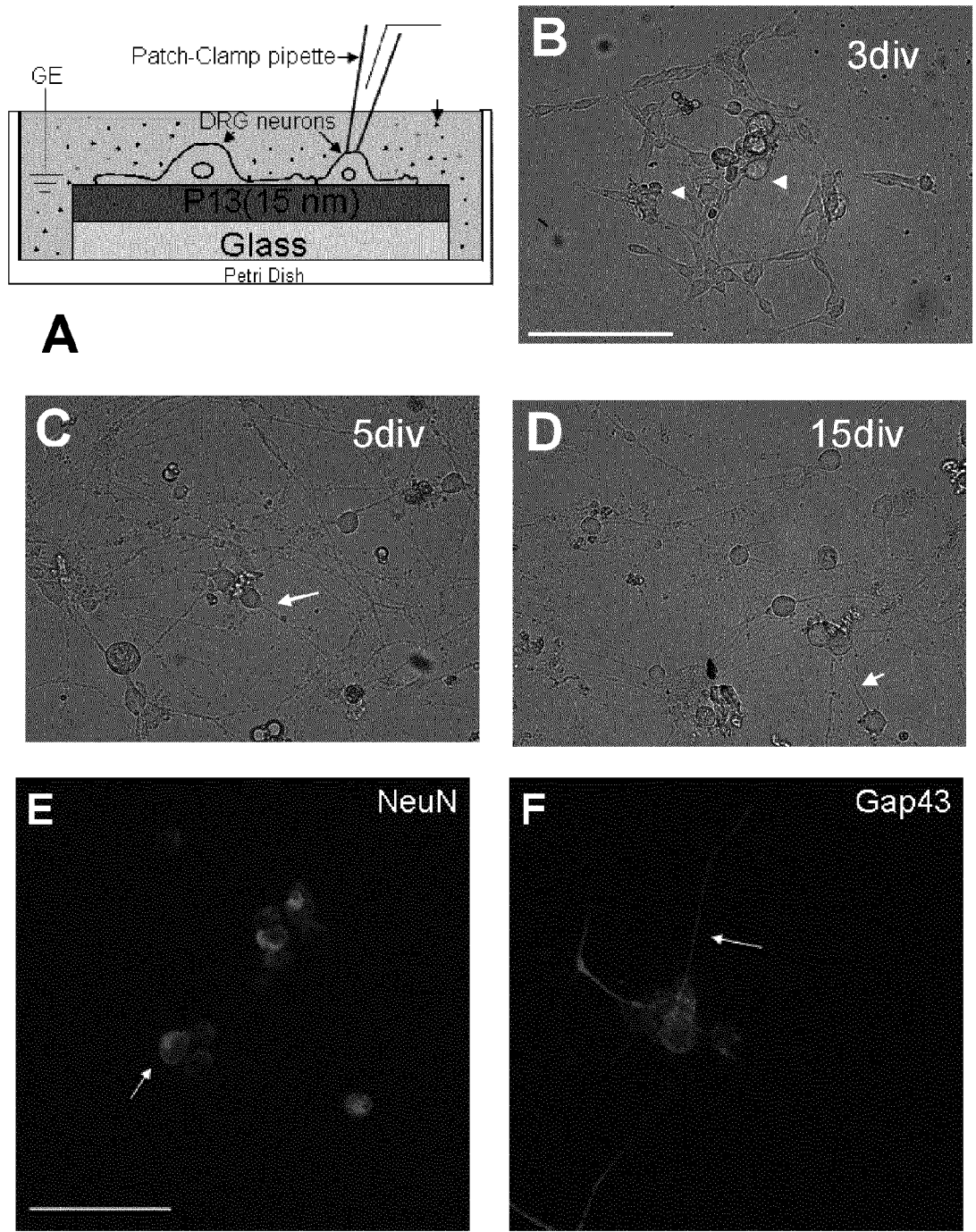
FIG. 3A shows the scheme for the verification of the neuronal cells in primary DRG culture, FIGS. 3B-3F the results of the experimental characterization.

Morphological observation after 3 days revealed that P13-PDL+Laminin cultured cells were characterized by the presence of spread neurons with different cell bodies diameter (FIG. 3B, arrows) and processes extension lining on a layer of glial cells. Marked neurite outgrowth was observed after 5 days in vitro (div) (FIG. 3C) evolving in dense network connection after several days (FIG. 3D).

EXAMPLE 2

To verify the presence of neuronal cells in primary DRG culture, we perform immunofluorescent staining by use of antibody against Neuronal Nuclear protein (NeuN), typical marker expressed by mature neuron. Single plane confocal imaging of NeuN positive cells from PDL+laminin (FIG. 3E) revealed that most of the rounded up cells with morphological phenotype reported for DGR neurons were NeuN positive cells.

Growth-associated protein GAP-43 is a typical axonal growth marker that is expressed in cell bodies and outgrowing neurites of fetal and neonatal rat brain and DRG sensory neuron. Representative confocal images of immunostaining of GAP43 from P13 cultured cells after 5 div, showed in FIG. 3F, indicated that high level of expression of GAP43 was evident in cell body and neuritis of DRG neurons, confirming the occurrence of axonal differentiating/regenerating processes in cells cultured on PDL+Laminin coated P13 thin films.

DRG culture plated on different P13-coated coverslips were fixed with 4% p/v paraformaldehyde in 0.1 M phosphate-buffered saline (PBS) for 10-15 min at room temperature (RT, 20-24° C.). After blocking with 3% bovine serum albumin (BSA) in PBS for 15 min at RT, cells were incubated overnight with mouse anti-NeuN (Millipore) or mouse-anti-GAP43 (Sigma-Aldrich, Milan, Italy) affinity-purified antibodies diluted 1:100 in blocking solution to which 0.1% Triton X100 was added. The day after, cells were incubated, respectively, with Alexa Fluor 488-conjugated donkey anti-mouse or Alexa Fluor 595-conjugated donkey anti-mouse antibodies (Molecular Probes-Invitrogen, Carlsbad, Calif., USA) diluted 1:1000 in blocking solution containing 0.1% Triton X100. Coverslips were next mounted with Prolong Anti-Fade (Molecular Probes-Invitrogen) and confocal laser scanning microscopy (CLSM) investigation was carried by a Nikon Eclipse 2000-E laser scanning confocal microscope in backscattering conditions equipped with with a 40× or 60× oil-objective and 400 nm diode, 488 nm $Ar^+$ and 543 nm He—Ne lasers as exciting sources.

EXAMPLE 3

Figure 4:
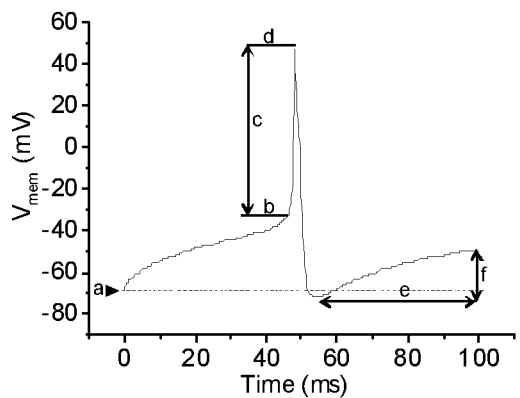
FIG. 4 shows the results of various characterization of DRG neuron electrophysiological properties.
Figure 4:
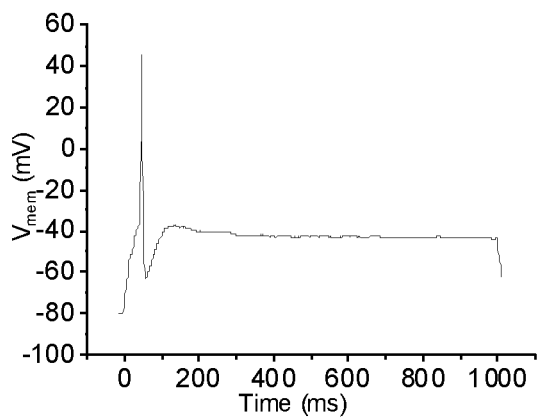
Figure 4:
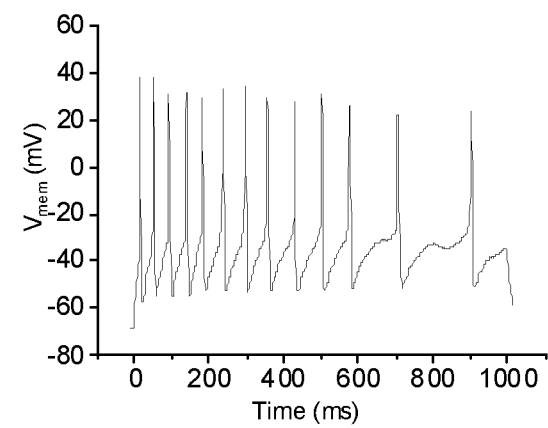

The effect of P13 thin-films was also characterized with regards to DRO neuron electrophysiological properties. To this end we carried out whole-cell patch-clamp experiments on DRG neuron after 10-12 days in culture on PDL+Laminin coated P13 thin films (FIG. 4). Since DRG primary neuron are a heterogeneous population, effort has been put to choose neurons with a small diameter (<30 µm) [5].

All the electrophysiological data we collected indicated that plating on P13+PDL-laminin preserve the functionality of DRG neurons, with values in line with those reported previously for this cell culture type.

Current recordings were obtained with the whole-cell configuration of the patch-clamp technique. Patch pipettes were prepared from thin-walled borosilicate glass capillaries to have a tip resistance of 2-4 MΩ when filled with the standard internal solution. Membrane currents were amplified (List EPC-7) and stored on a computer for off-line analysis (pClamp 6, Axon Instrument and Origin 6.0, MicroCal). Because of the large current amplitude, the access resistance (below 10 MΩ) was corrected 70-90%. Experiments were carried out at RT (20-24° C.). Action potential (AP) and neuronal firing properties were recorded in Current Clamp mode by injecting repetitive increasing current pulse from −0.05 to 0.350 nA of 100 ms duration. Capacitative transient was compensated by nulling circuit of the recording amplifier. Resting membrane potential (Vmem) was measured 1 min after a stable recording was obtained (FIG. 4A). The threshold current ($I_{th}$) was defined as the minimum current required to evoke an AP. The AP voltage threshold ($V_{th}$, FIG. 4A b) was defined as the first point on the upstroke of an AP. The AP amplitude (FIG. 4A c) was measured between the peak (FIG. 4A d) and AP threshold level. The AP rising time to peak was defined as the time for rising from baseline to the AP peak. The after hyperpolarization (AHP) amplitude (FIG. 4A f) was measured between the maximum hyperpolarization and the final plateau voltage and AHP duration was the time between these two point (FIG. 4A f). Any cells without AP were excluded from the study.

The maximal number of firing was calculated by counting number of overshooting AP in response to a 1 s pulse of current injection. Whole-cell current-voltage (I-V) curves for individual neurons were generated by calculating the mean peak inward current at each test potential (see below) and normalized for the relative cell capacitance values.

EXAMPLE 4

With control intracellular and extracellular saline, cells were held at −60 mV and family of increasing current pulses of 50 pA were injected from 50 to 350 pA amplitude for a duration of 100 ms (FIG. 4A) or 1 s (FIG. 4B-C). Of note, the neuronal depolarization and generation of action potential occurs in response to threshold current injection. In line with previous studies, firing pattern of patched neurons was variable: single action potential (phasic firing) (FIG. 4B) as well as repetitive firing (FIG. 4C) neurons were observed upon long lasting pulse stimulation (1 s).

Analyses of the mean of different bioelectrical properties recorded in several neurons patched is reported in Table 1.

The passive membrane properties that we analyzed were the cell Capacitance and the Resting membrane potential (Vmem). Mean of cell capacitance as well as Resting Vmem values we recorded were in line with what expected for DRG neuron of small diameter (≤30 μm). Excitability parameters measured includes the AP threshold current ($I_{th}$) and the AP Voltage threshold ($V_{th}$), the AP peak and amplitude, time to peak, number of firing per second and after hyperpolarization period (AHP) amplitude and duration.

cell culture treatment is reported. In particular, $V_{DS}$ is the voltage between the source and drain electrodes while $V_{GS}$ is the voltage between the source and the gate electrodes. The locus curves reported in left panels are obtained by varying $V_{GS}$ from 0V to 100V and keeping $V_{GS}=V_{DS}$, while the output curves reported in the right panels are obtained by varying $V_{DS}$ from 0V to 100V and keeping $V_{GS}$ constant for each curve.

TABLE 1 electrophysiological properties of DRG neuron plated on P13. Values reported are mean ± SE. AP, action potential, AHP, after hyperpolarization potential (n = 16 for all parameters and n = 8 for AHP).

| Cp (pF) | Resting V mem (mV) | Ith (nA) | Vth (mV) | Peak amplitude (mV) | Time to peak (ms) | AP (mV) | AHP Amplitude | AHP Duration (ms) | Max AP number |
|---|---|---|---|---|---|---|---|---|---|
| 25.6 ± 2.2 | −69.3 ± 2.7 | 0.09 ± 0.005 | −26.8 ± 3.8 | 45.3 ± 4.1 | 3.1 ± 0.5 | 72 ± 5.5 | 20.5 ± 2.5 | 38.2 ± 3.3 | 4.4 ± 1.4 |

EXAMPLE 5

Also the effect of "in vitro cell culturing" on performance of P13-based OFET device was characterized.

It is well known, in fact, that in general organic materials suffer from exposure to oxygen and moisture, which promote charge trapping and ultimately induce severe device performance degradation. If this were the case, we would have found a system that is suitable for functional growth of neuronal network, but not as a bio-compatible field effect electronic platform.

Figure 2:
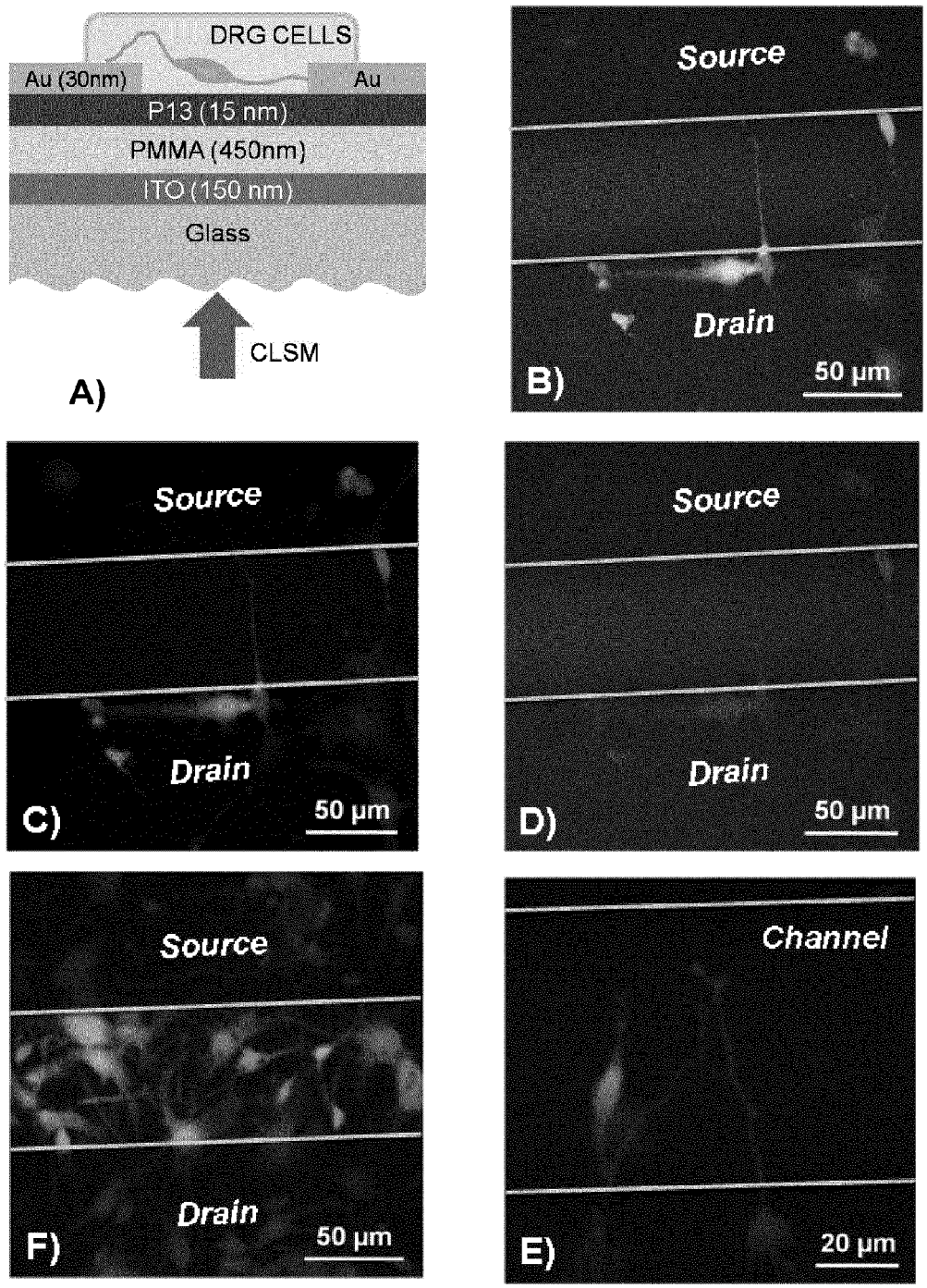
FIG. 2A shows a simplified scheme for an OFET according to the present invention, FIG. 2B-2F the photoluminescent emission in different portions of the device.

In order to verify the compatibility of our device with cell culture conditions, we plated DRG neuronal primary culture directly on PDL+laminin coated bottom-gate/top-contact P13 OFETSs (FIG. 2A). The device with drops-bathed cells on the top was kept in biological incubator, at 37° C. and 5% $CO_2$ and 95% of humidity, standard in vitro condition used to ensure proper growth and maintenance of biological sample. CLSM investigation was performed collecting PL signal through the glass/ITO/PMMA substrate. In FIG. 2 we report single plane confocal images of FDA (Fluorescein Diacetate) assay performed after 5 div, which indicated that living cells with morphological phenotype of differentiated DRG neuron were grown on P13-based device. It is interesting to note that performing CLSM in backscattering condition and through the device transparent substrate we were able to observe the presence of living cells grown not only on the P13 device active area but also on the gold contacts.

Since the PL emissions of the device active material and of FDA assay are spectrally well-separated (red and green emission centred at distinct CLSM photomultiplier detection channels, respectively) the merge of the single-channel CLSM images (FIG. 2B-D) confirms that the spectral and morphological characteristics of the P13 film has not been modified by the interaction with the DRG neuronal primary culture. Moreover, the green emission is almost completely localized in the neuronal cells. Interestingly, neurite projection from the gold electrode to the device active layer was observed (FIG. 2E). Moreover dense network of glial cells supporting neurons was also observed in different part of the device (FIG. 2F).

EXAMPLE 6

Figure 5:
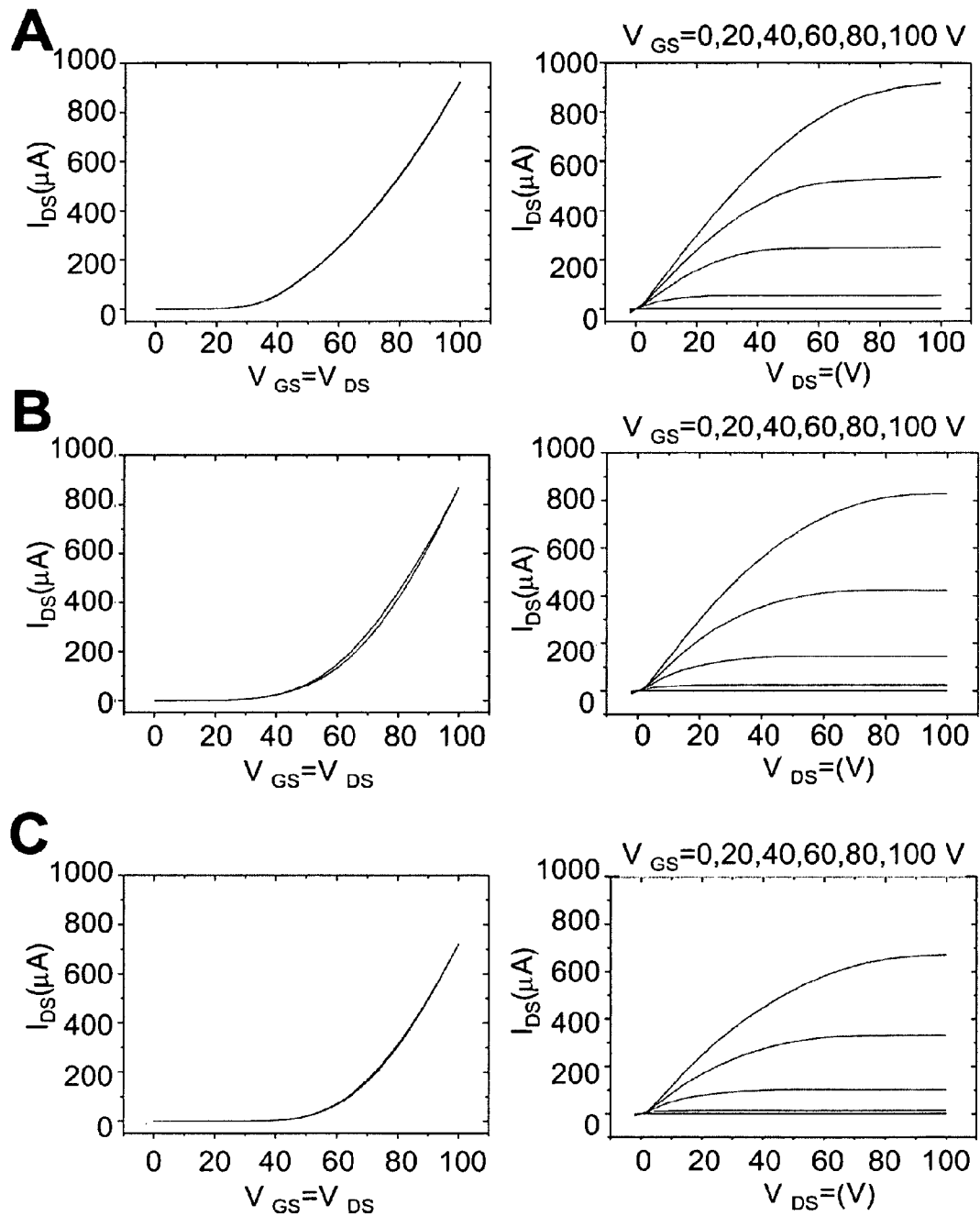
FIGS. 5A-5C shows the electrical characterization of a P13 OFET before and after cell culture treatment.

In FIG. 5 electrical characterization of the perylene OFET before (FIG. 5A) and after 6 days (5B) and 16 days (5C) of Threshold voltage and electron mobility values calculated from the locus curves at every time point are reported in Table 2.

TABLE 2

Charge mobility ($\mu_n$) and Voltage threshold ($V_{th}$) of device before and after 6 or 16 days in vitro (div)

| Time point (div) | $\mu_n$ (cm²/Vs) | $V_{th}$ (V) |
|---|---|---|
| 0 | 0.17 | 15 |
| 6 | 0.24 | 31 |
| 16 | 0.20 | 34 |

Surprisingly the P13-OFET is still perfectly performing after 16 div. Electron mobility values ($\mu_n$) are not affected by the culture treatments and compare favourably with the mobility value reported for top-contact/bottom-gate OFET based on PTCDI-C13 grown on $SiO_2$ functionalized with a PMMA thin-layer (1.3 nm).

Threshold voltage values ($V_{th}$) increase after 6 div whereas it remains constant from 6 div to 16 div. Electrical curves hysteresis is absent at any time point. The absence of the phenomenon of stress in OFETs together with the nearly invariance of charge carrier mobility make us suppose that the degradation of the devices is likely correlated to organic/metal interface that determine the charge injection process. Indeed, we observe an incipient pinhole and damage formation on the gold contacts after several water washing. This problem can be prevented by capping the metal contacts with a highly hydrophobic layer.

Examples 5 and 6 show that the OFET is fully compatible with the environment and the biomedical application, meaning that the device does not degrade or interfere with the growth of the biological sample (results of example 5) and that the OFET is still well performing even after 16 days of exposure to the conditions for cell culture treatment (results of Example 6)

EXAMPLE 7

The purpose of this example is to evaluate the performance of the P13 OFET by operating it while in a saline physiological solution. Although the system is capable to operate for short times, it shows a degrade in its electrical performaces, in particular is has been detected a high drain-source current for low gate voltages (Vg=12V). This phenomena has been associated with a detrimental interaction of the drain and source electrodes material with the saline solution.

So this example shows that the OFET can be successfully operated in this environment, but only for a limited amount of time, even though its compatibility with the system is much more prolonged (as per results of example 6) if the device is not turned on, or turned on at given times, such as when the device is used as diagnostic tool.

EXAMPLE 8

An OFET device is fabricated as in the case of example 1, but in this case on top of both the source and drain electrodes and the P13 layer a further overcoating capping layer is deposited with the purpose of protecting and enhancing the device performances over time when operated in a saline environment.

Figure 6A:
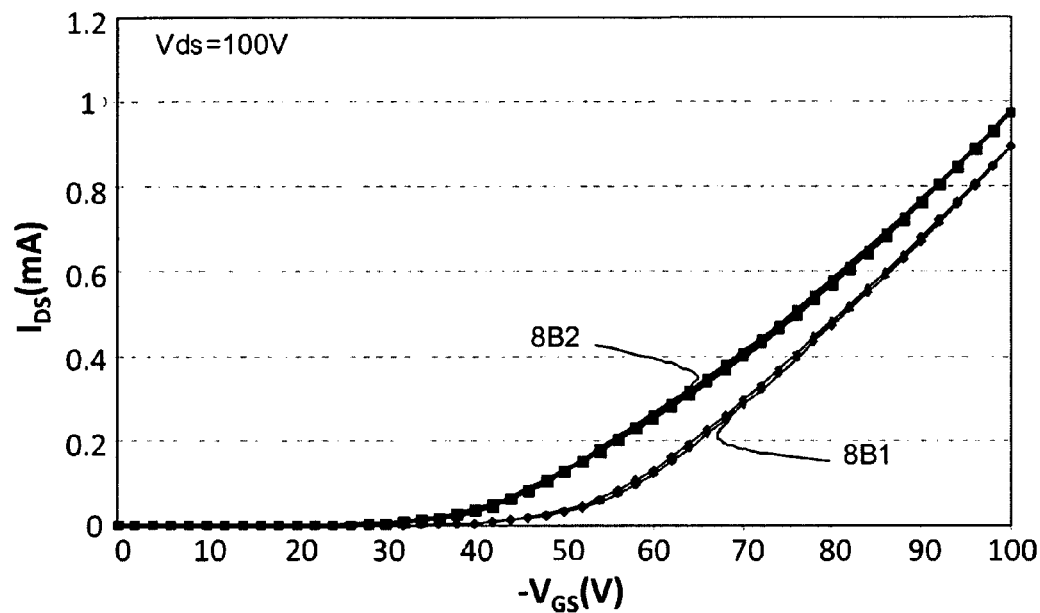
FIGS. 6A and 6B show a comparison of the transfer curves of n-type charges for OFETs according to the present invention, before and after being capped with a suitable organic layer.
Figure 6B:
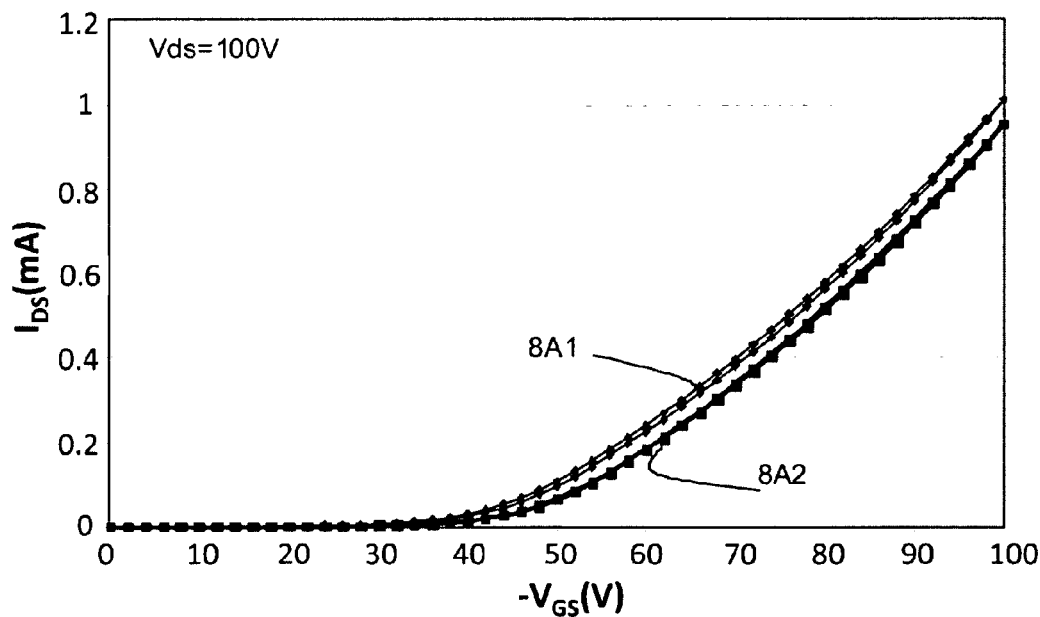

Two different devices are made with a capping layer having a maximum thickness of 50 nm, device 8A is made with a P13 capping layer, device 8B (comparative) with a pentacene capping layer. In FIGS. 6A and 6B are shown the comparison of the transfer curves for the n-type charges for the devices 8A and 8B before (8A1, 8B1, normal line) and after (8A2, 8B2, thicker line) the deposition of the capping layer.

These curves shows that there is no meaningful impact on the transfer curves for the n-type charge carriers of the devices.

EXAMPLE 9, COMPARATIVE

An OFET device 9 is fabricated as in the case of example 1, but instead then using P13, pentacene has been used as the organic semiconductor layer placed in contact with the source and drain electrodes and the PMMA dielectric layer.

Figure 7:
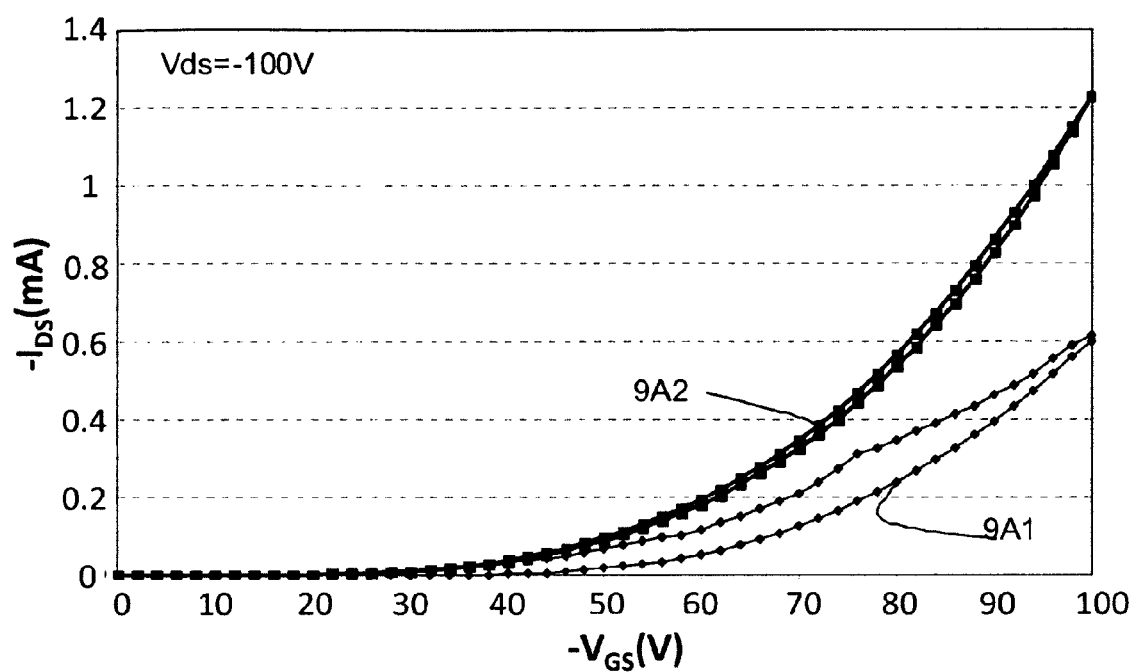
FIG. 7 shows a comparison of the transfer curves of p-type charges OFET not according to the present invention, before and after being capped with a suitable organic layer.

In this case the device is covered with a capping layer of P13 having a maximum thickness of 50 nm. As per the case of example 8, in FIG. 7 is shown the comparison of the transfer curves, in this case for the p-type charge carriers, so in the X axis minus Vgs is plotted and on the Y axis minus Ids is plottd, this due to the nature of the pentacene layer; line 9A1 (normal thickness) represents the p-transfer curve before the addition of the capping layer, line 9A2 (thicker line), after.

Also in this case there is an impact deriving from the addition of the organic capping layer, but the device operational parameters are still acceptable.

EXAMPLE 10

Having verified that the capping layers do not interfere with the devices electrical characteristics, device 8A has been operated in a saline environment, in a saline environment with neurons deposited on the P13 capping layer, and in a saline environment with neurons and Capsazepine (pharmacological agent, modulator of the neuronal activity) deposited on the P13 capping layer.

The OFET is supplied with a gate voltage ranging from 0 to 1 V in 0.02 increments every 0.2 msec and keeping a constant drain-source voltage of 1V.

Figure 8A:
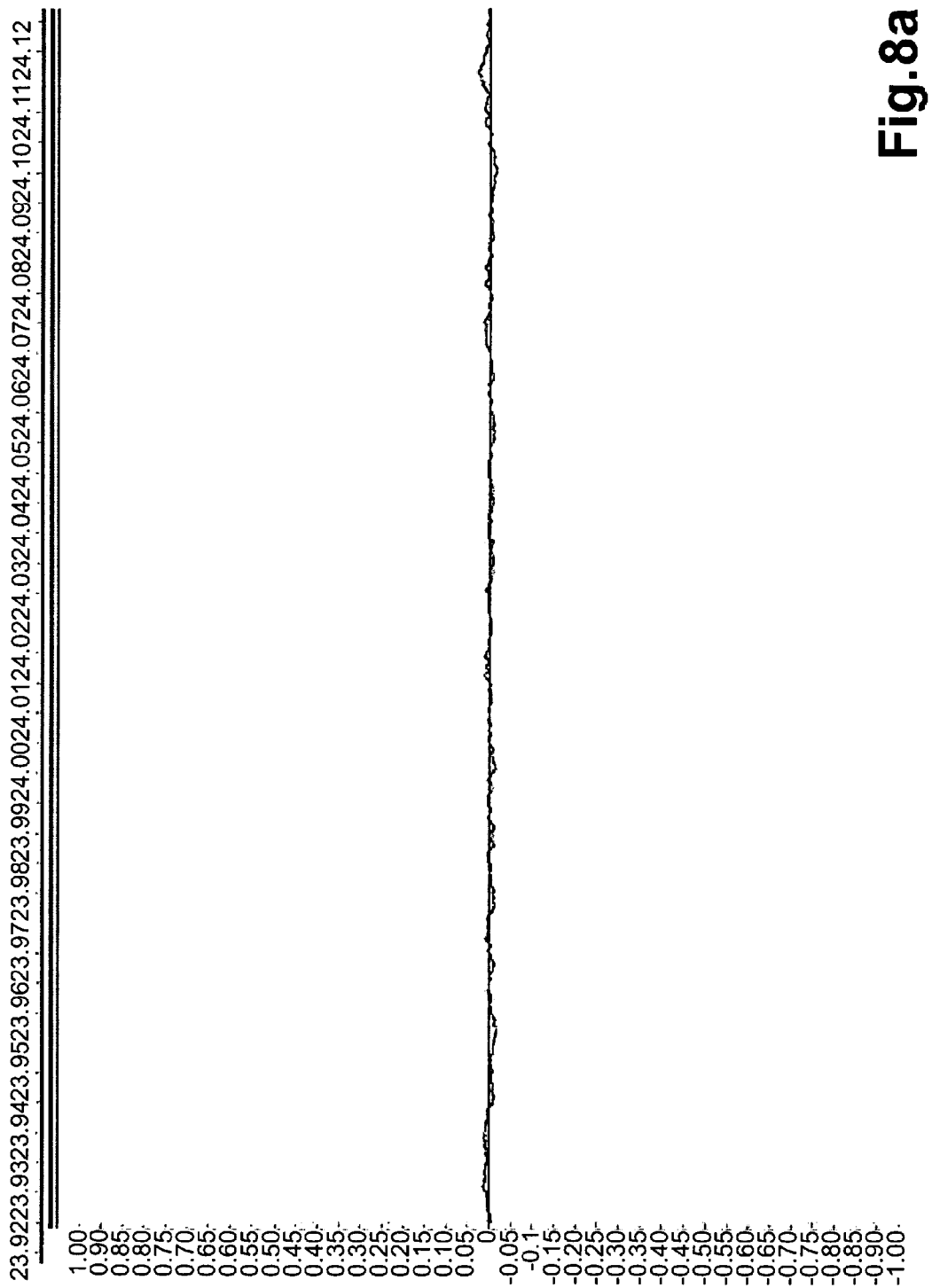
FIGS. 8A-8D show the results of cellular stimulation for a P13 capped OFET realized according to the present invention.
Figure 8B:
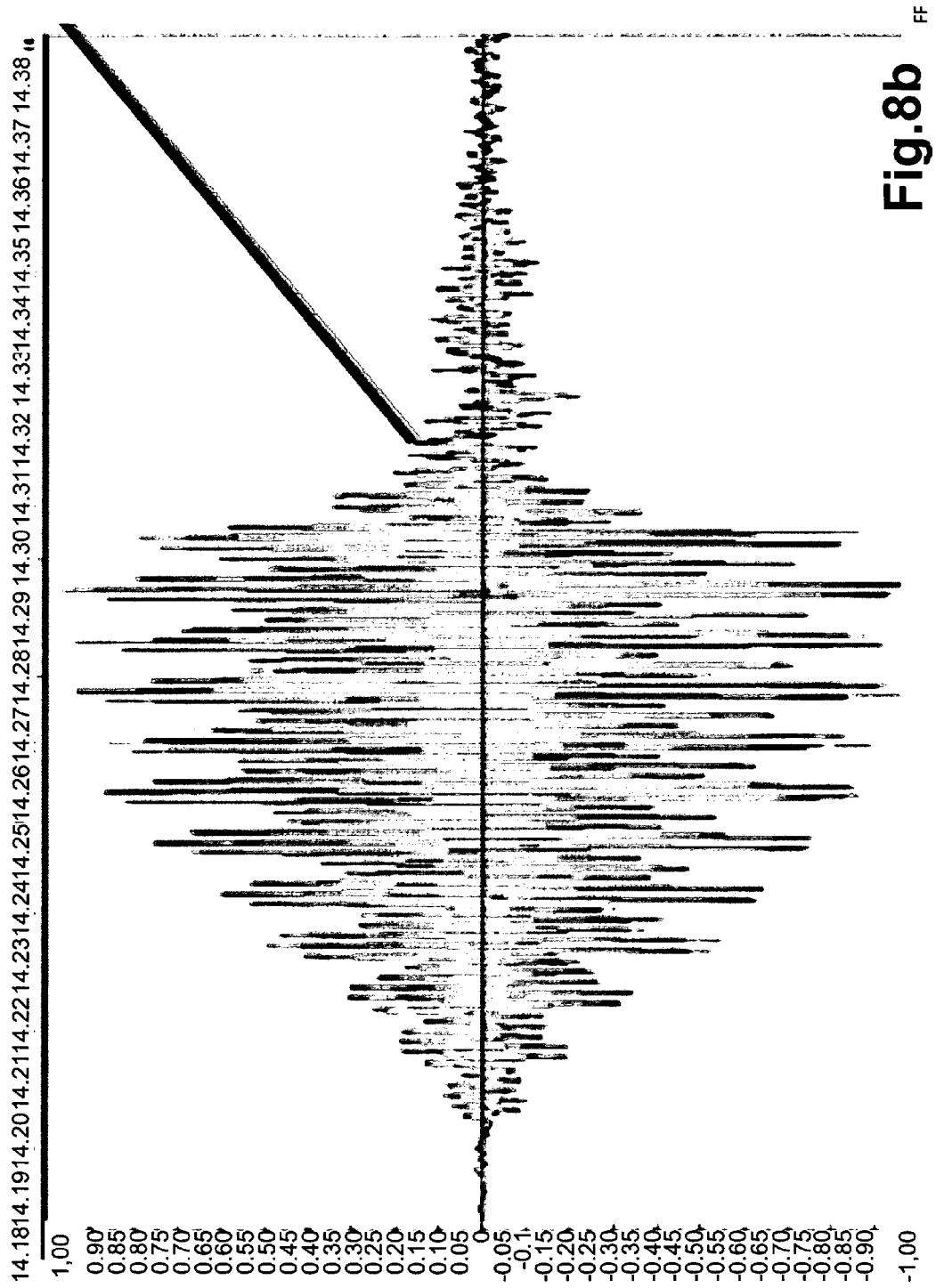
Figure 8C:
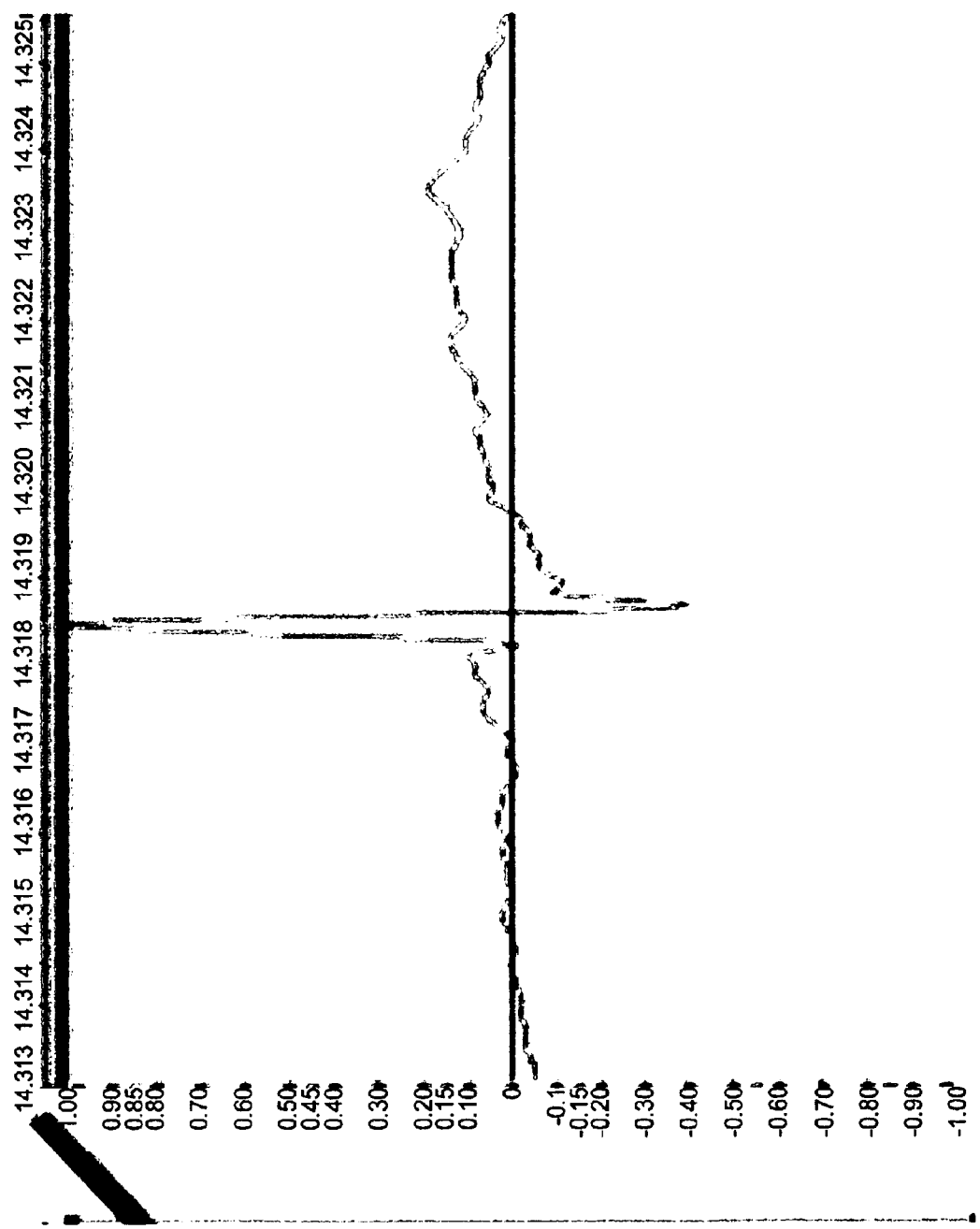
Figure 8D:
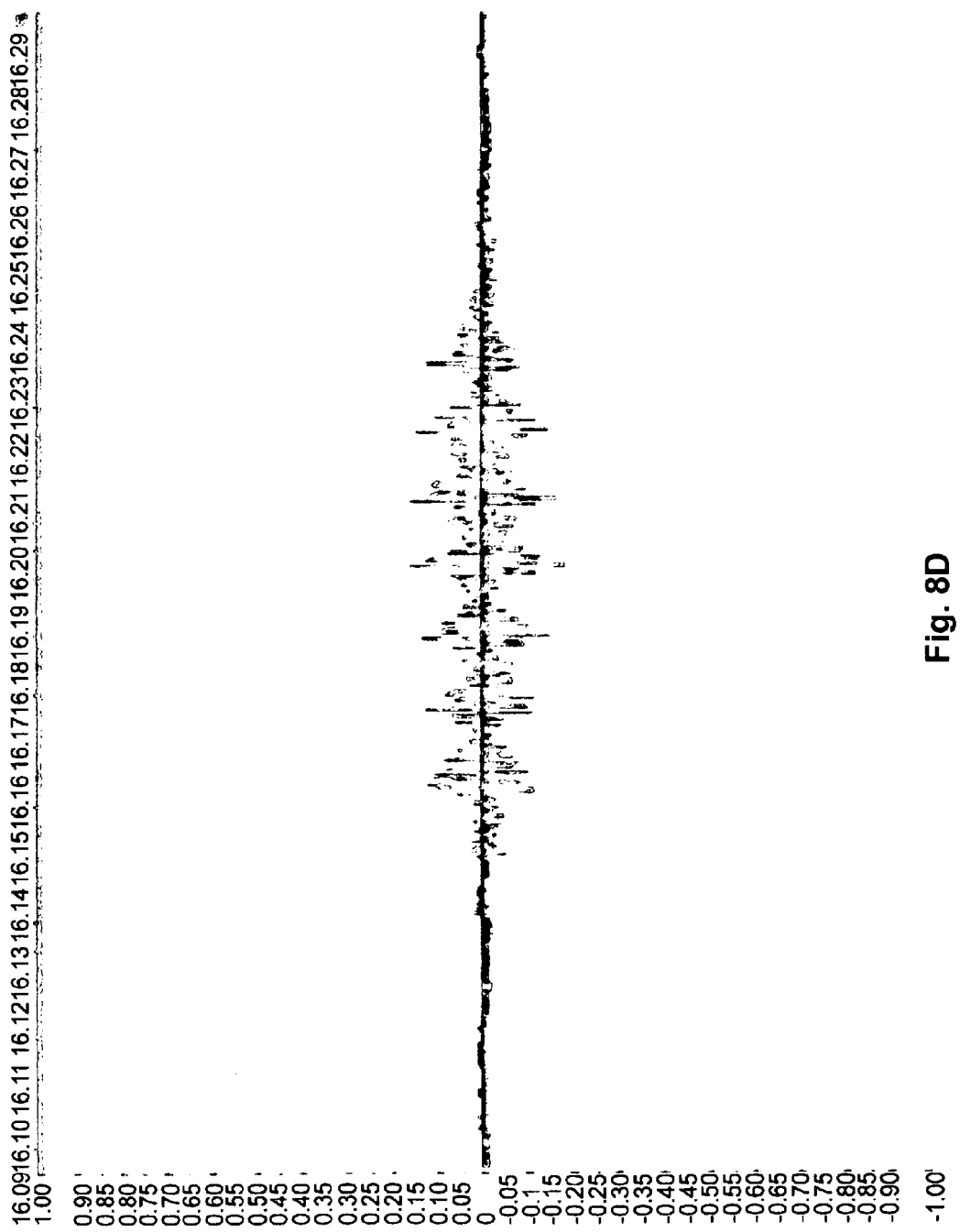

The electrical output of the device is recorded and depicted in FIGS. 8A (saline only), 8B (saline+neurons), 8D (saline+neurons+Capsazepine). On the side of FIG. 8B, shown as FIG. 8D, is present an expanded view of a single signal taken at a given voltage of 0.8V.

It is possible to observe that the device is capable both to stimulate and record the effects of the stimulation on the neurons as well as to observe the effect of the added medical agent.

EXAMPLE 11

Figure 9:
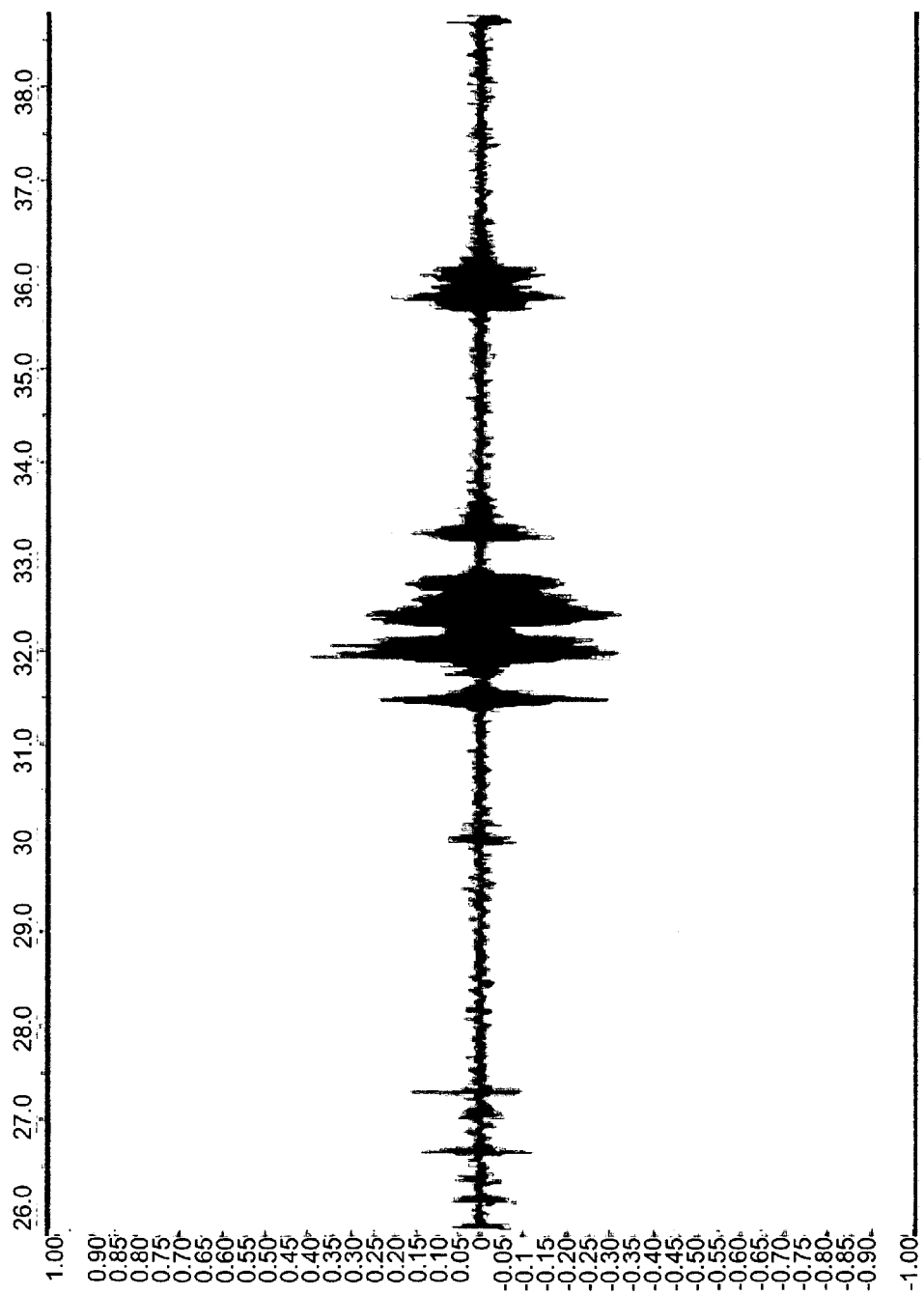
FIG. 9 shows the results of cellular stimulation for a pentacene capped OFET realized according to the present invention.

Device 8B has been tested in the same condition of device 8A obtaining very similar results, in this case the only plot shown, in FIG. 9, is the one obtained with (saline+neurons).

Example 10 and example 11 show the equivalency of pentacene and P13 (as chosen representative of the diimmide perylene derivative (PTCDI) substituted with alkyl groups on the Nitrogen atoms according to formula (I) family) as capping layers.

EXAMPLE 12, COMPARATIVE

Figure 10:
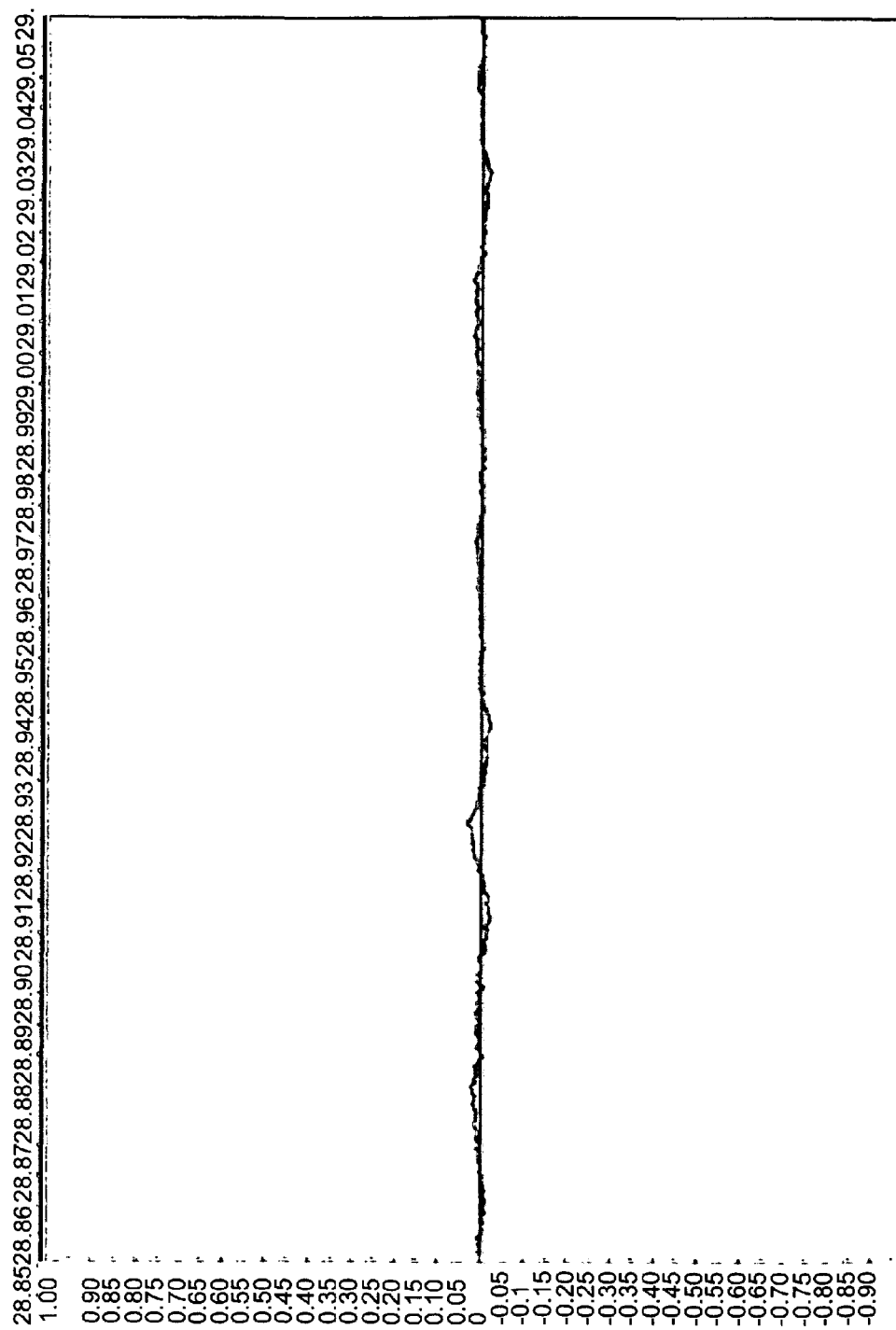
FIG. 10 shows the results of cellular stimulation for a P13 capped OFET not realized according to the present invention.

Also device 9 has been tested in the conditions outlined in example 11 (saline+neurons), but in this case no meaningful signal is recored as it is possible to observe from FIG. 10.

This results shows that even the presence of a suitable capping layer, such as a layer of P13, is not capable to render operative an OFET when the organic semiconductor layer is not a diimmide perylene derivative (PTCDI) substituted with alkyl groups on the Nitrogen atoms according to formula (I).

The invention claimed is:

1. A device comprising an organic field effect transistor (OFET) with charge injecting contacts characterized in that said organic field effect transistor contains a semiconductor layer formed by a diimmide perylene derivative (PTCDI), substituted with alkyl groups at the Nitrogen atoms, according to formula (I)

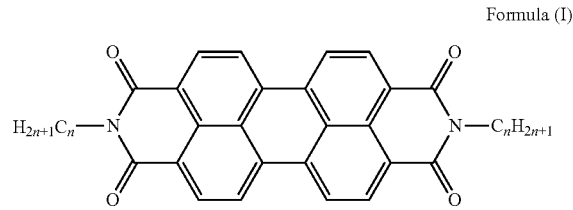

Formula (I)

comprising a capping layer, deposited to cover said charge injecting contacts, of an organic compound selected in the group consisting of diimmide perylene derivative (PTCDI), substituted with alkyl groups at the Nitrogen atoms, according to formula (I) and pentacene.

2. The device according to claim 1 wherein the two alkyl groups at the Nitrogen atoms are n-alkyl groups having the same number of carbon atoms.

3. The device according to claim 2 wherein said n-alkyl groups have 5, 8, 12, 13, 14 or 18 carbon atoms.

4. The device according to claim 1 wherein said diimmide perylene derivative (PTCDI), substituted with alkyl groups at the Nitrogen atoms, according to formula (I) is N,N'-ditridecylperylene-3,4,9,10-tetracarboxylic diimide (P13).

5. The device according to claim 1 wherein said capping layer is made of N,N'-ditridecylperylene-3,4,9,10-tetracarboxylic diimide (P13).

6. The device according to claim 1 wherein said capping layer has uniform thickness.

7. The device according to claim 1 wherein said capping layer has a maximum thickness comprised between 35 and 100 nm.

8. The device according to claim 7 wherein said maximum thickness is comprised between 40 and 70 nm.

9. The device according to claim 1 wherein a framing deposit of an inert material is present on said capping layer, in correspondence of the OFET boundaries.

10. The device according to claim 1 wherein said device is a medical sensor.

11. The device according to claim 1 wherein said device is a medical cell stimulator.

12. The device according to claim 1 wherein said device is at the same time a medical sensor and a medical cell stimulator.

13. The device according to claim 1 wherein said organic field effect transistor is an organic light emitting transistor.

14. A method comprising:
providing the device according to claim 10; and
using the device as an in vitro sensing system of biological cellular activity.

15. A method comprising:
providing the device according to claim 11; and
using the device as an in vitro stimulator for biological cellular activity.

16. A method comprising:
providing the device according to claim 12; and
using the device as an in vitro stimulator for biological cellular activity and as an in vitro sensing system of biological cellular activity.

17. The method according to claim 14 wherein said biological cellular activity is neuronal.

18. A method of monitoring biological cellular activity comprising the steps of:
providing the device according to claim 10;
depositing a biological cellular material on said diimmide perylene derivative (PTCDI), substituted with alkyl groups at the Nitrogen atoms, according to formula (I);
contacting said device with an aqueous based system; and
monitoring the activity of said biological cellular material.

19. A method of stimulating biological cellular activity comprising the steps of:
providing a device according to claim 11;
depositing a biological cellular material on said diimmide perylene derivative (PTCDI), substituted with alkyl groups at the Nitrogen atoms, according to formula (I);
contacting said device with an aqueous based system; and
driving the device to stimulate the activity of said biological cellular material.

20. A method of stimulating biological cellular activity and monitoring said biological cellular material, comprising the steps of:
providing a device according to claim 12;
depositing a biological cellular material on said diimmide perylene derivative (PTCDI), substituted with alkyl groups at the Nitrogen atoms, according to formula (I);
contacting said device with an aqueous based system;
driving the device to stimulate the activity of said biological cellular material; and
monitoring the activity of said biological cellular material.

21. The method according to claim 18 wherein said biological cellular material comprises neurons.

* * * * *